United States Patent
Kitano et al.

(10) Patent No.: US 10,381,963 B2
(45) Date of Patent: Aug. 13, 2019

(54) MOTOR DRIVE CONTROLLING APPARATUS, MOTOR DRIVE CONTROLLING METHOD, AND TUBE PUMP

(71) Applicant: MINEBEA MITSUMI INC., Nagano (JP)

(72) Inventors: Takamichi Kitano, Kakegawa (JP); Masaaki Nagai, Yokohama (JP); Akira Muto, Fujisawa (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 15/445,047

(22) Filed: Feb. 28, 2017

(65) Prior Publication Data

US 2017/0264223 A1    Sep. 14, 2017

(30) Foreign Application Priority Data

Mar. 10, 2016 (JP) ................. 2016-047013

(51) Int. Cl.
*H02P 7/00* (2016.01)
*H02P 6/17* (2016.01)
(Continued)

(52) U.S. Cl.
CPC ............ *H02P 6/17* (2016.02); *A61M 1/1039* (2014.02); *A61M 1/1046* (2013.01);
(Continued)

(58) Field of Classification Search
CPC .... H02P 6/17; H02P 6/06; H02P 23/03; H02P 2205/07; H02P 27/08; A61M 1/1039;
(Continued)

(56) References Cited

U.S. PATENT DOCUMENTS 3,607,082 A * 9/1971 Thiers ................. B01L 3/021
141/18
4,350,941 A * 9/1982 McClure ............. G05B 19/232
318/603
(Continued)

FOREIGN PATENT DOCUMENTS

CN         1992506 A      7/2007
DE      3922686 A1      1/1991
(Continued)

OTHER PUBLICATIONS

Extended European Search Report dated Dec. 20, 2017 for corresponding European Application No. 17159290.0.
(Continued)

*Primary Examiner* — Rina I Duda
(74) *Attorney, Agent, or Firm* — Pearne & Gordon LLP

(57) ABSTRACT

A motor drive controlling apparatus includes a controller that generates a drive control signal in response to input of a speed command signal and a motor driver that generates a drive signal in response to input of the drive control signal and outputs the drive signal to a motor, and the controller repeatedly generates the drive control signal in a period during which the speed command signal is inputted and stops generating the drive control signal in a period during which the speed command signal is not inputted to repeat an operation period in which the motor performs rotational operation and a stop period in which the motor stops operating in a non-excited state.

12 Claims, 10 Drawing Sheets

(51) Int. Cl.
*A61M 1/10* (2006.01)
*H02P 27/08* (2006.01)
*H02P 6/06* (2006.01)
*H02P 23/03* (2006.01)

(52) U.S. Cl.
CPC ............ *A61M 1/1086* (2013.01); *H02P 6/06* (2013.01); *H02P 23/03* (2013.01); *H02P 27/08* (2013.01); *H02P 2205/07* (2013.01)

(58) Field of Classification Search
CPC . A61M 1/1046; A61M 1/1086; B60K 31/047; B60W 2050/021
USPC .................................. 318/452, 599, 811, 443
See application file for complete search history.

(56) References Cited

U.S. PATENT DOCUMENTS

| | | | |
|---|---|---|---|
| 4,487,604 A | 12/1984 | Iwatschenko et al. | |
| 4,919,650 A | 4/1990 | Feingold et al. | |
| 4,969,808 A * | 11/1990 | Tsukada | F04B 43/1253 417/477.1 |
| 5,062,775 A * | 11/1991 | Orth | A61M 1/10 417/319 |
| 5,801,509 A * | 9/1998 | Sawa | H02P 6/16 318/603 |
| 6,254,567 B1 * | 7/2001 | Treu | A61M 1/1696 604/29 |
| 6,737,860 B2 * | 5/2004 | Hsu | H05K 7/20209 324/161 |
| 6,984,956 B2 * | 1/2006 | Kang | H02P 8/22 318/685 |
| 7,633,256 B2 * | 12/2009 | Reichert | G02B 26/122 318/602 |
| 8,267,881 B2 * | 9/2012 | O'Mahony | A61M 1/34 210/645 |
| 8,585,635 B2 * | 11/2013 | Degen | A61M 1/285 604/29 |
| 8,963,469 B2 * | 2/2015 | Bates | H02P 27/08 318/496 |
| 8,981,695 B2 * | 3/2015 | Bates | H02P 27/08 318/400.41 |
| 8,988,031 B2 * | 3/2015 | Bates | H02P 25/18 318/495 |
| 9,190,940 B2 * | 11/2015 | Markham | H02P 6/08 |
| 9,465,370 B2 * | 10/2016 | Alexander | H02P 29/02 |
| 9,748,875 B2 * | 8/2017 | Arabackyj | H02P 6/12 |
| 2006/0197489 A1 * | 9/2006 | Nakai | F16H 61/32 318/701 |
| 2007/0152625 A1 | 7/2007 | Son | |
| 2008/0152327 A1 * | 6/2008 | Oh | H02P 6/182 388/815 |
| 2011/0031906 A1 * | 2/2011 | Yasohara | G06F 13/4256 318/66 |
| 2012/0100023 A1 * | 4/2012 | Hanazuka | F04B 43/1276 417/477.7 |
| 2013/0267883 A1 * | 10/2013 | Medrano | A61G 7/015 604/5.01 |
| 2014/0049199 A1 | 2/2014 | Ishizuka et al. | |
| 2014/0084832 A1 * | 3/2014 | Sato | H02P 27/08 318/452 |
| 2014/0132189 A1 * | 5/2014 | Kim, II | G03G 15/55 318/400.13 |
| 2015/0233367 A1 * | 8/2015 | Shimogata | F04B 43/1253 417/412 |
| 2016/0156299 A1 * | 6/2016 | Romanowich | H02P 29/0241 318/400.21 |
| 2016/0365819 A1 * | 12/2016 | Masuda | H02P 6/08 |

FOREIGN PATENT DOCUMENTS

| | | | |
|---|---|---|---|
| EP | 0825708 A2 | 2/1998 | |
| EP | 1 804 370 A2 | 7/2007 | |
| EP | 2 698 914 A2 | 2/2014 | |
| JP | 56-94991 A | 7/1981 | |
| JP | 01-291690 A | 11/1989 | |
| JP | 03-11397 U | 2/1991 | |
| JP | H10-66392 A | 3/1998 | |
| JP | H10-290831 A | 11/1998 | |
| JP | 2007-002764 A | 1/2007 | |
| JP | 2008-067560 | * 3/2008 | ............. B41J 19/18 |
| JP | 2008-067560 A | 3/2008 | |
| JP | 2008-208808 A | 9/2008 | |
| JP | 2011-125148 A | 6/2011 | |
| JP | 2015-146728 A | 8/2015 | |

OTHER PUBLICATIONS

Information Statement dated May 21, 2018 in the corresponding Japanese Application No. 2016-047013 and English translation.
Japanese Office Action dated Jan. 23, 2018 in the corresponding Japanese Application No. 2016-047013 and English translation.
1st Chinese Office Action dated Feb. 28, 2019 for corresponding Chinese Application No. 201710130714.8 and English translation.

* cited by examiner

MOTOR DRIVE CONTROLLING APPARATUS, MOTOR DRIVE CONTROLLING METHOD, AND TUBE PUMP

CROSS REFERENCE TO RELATED APPLICATIONS

This application claims the benefit of Japanese Patent Application No. 2016-047013, filed on Mar. 10, 2016, which is hereby incorporated by reference in its entirety.

BACKGROUND

Technical Field

The present disclosure relates to a motor drive controlling apparatus, a motor drive controlling method, and a tube pump.

Background Art

There is a known tube pump of related art as a pump apparatus. In a tube pump, a roller is rotated by a motor to press and flatten a tube so as to deliver a liquid contained in the tube. The tube pump is used in a medical apparatus. For example, there is a known pump apparatus for artificial dialysis (blood pump) in which a brushless DC motor rotates a rotor having a roller.

For example, in the pump apparatus for artificial dialysis, a speed reducer is provided between the rotor and the brushless DC motor. The speed reducer is required to not only rotate the rotor in the blood pump at a low speed but also produce a large torque even in low-speed rotation. Japanese Patent Laid-Open Nos. 10-290831, 2015-146728, 2008-67560, and 10-66392 are examples of related art documents.

Some users desire to operate a pump apparatus for artificial dialysis, for example, at a rotational speed lower than that specified in the specifications of a motor used in the apparatus.

The present disclosure is related to providing a motor drive controlling apparatus, a motor drive controlling method, and a tube pump that allow a motor to perform rotational operation at a low rotational speed that does not fall within the specifications of the motor.

SUMMARY

In accordance with one aspect of the present disclosure, a motor drive controlling apparatus includes a controller that generates a drive control signal in response to input of a speed command signal and a motor driver that generates a drive signal in response to input of the drive control signal and outputs the drive signal to a motor, and the controller repeatedly generates the drive control signal in a period during which the speed command signal is inputted and stops generating the drive control signal in a period during which the speed command signal is not inputted to repeat an operation period in which the motor performs rotational operation and a stop period in which the motor stops operating in a non-excited state.

According to this aspect of the present disclosure, the motor is allowed to perform rotational operation at a low rotational speed that does not fall within the specifications of the motor.

DETAILED DESCRIPTION

Hereinafter, a motor drive controlling apparatus, a motor drive controlling method, and a tube pump according to an embodiment will be described with reference to the accompanying drawings.

(Embodiment)

Figure 1:
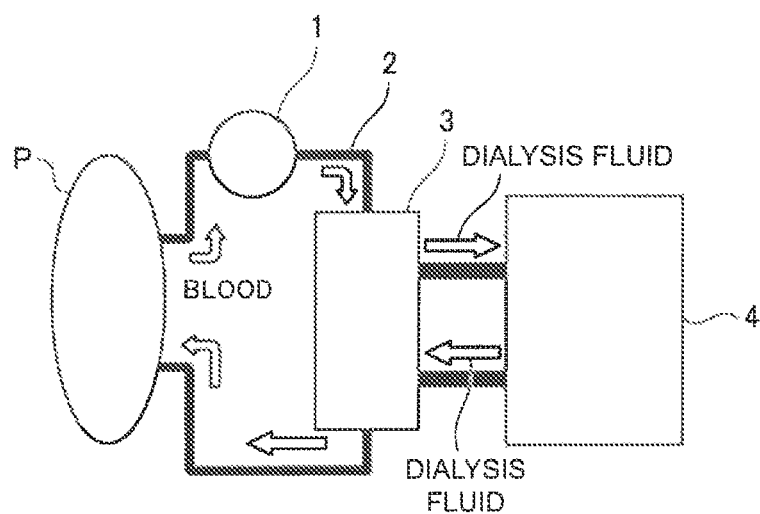
FIG. 1 is a diagram showing an example of a configuration of an artificial dialysis system into which a blood pump according to an embodiment of the present disclosure is assembled.

The following description will be made of a case where a tube pump in which a motor drive controlling apparatus according to the present embodiment is used is a blood pump in an artificial dialysis system. FIG. 1 shows an example of the configuration of the artificial dialysis system into which the blood pump according to the present embodiment is assembled.

The artificial dialysis system shown in FIG. 1 includes a blood pump 1, a dialyzer 3, and a dialysis fluid supplier 4. The blood pump 1 transports the blood of a patient P via a tube 2 to the dialyzer 3 (blood removal). The dialyzer 3 uses a semipermeable membrane and a dialysis fluid supplied from the dialysis fluid supplier 4 to remove wastes from the blood of the patient P, maintains an electrolyte in the blood, and maintains the amount of water in the blood. The blood pump 1 causes the blood processed by the dialyzer 3 to return to the patient P via the tube 2 (retransfusion).

Figure 2:
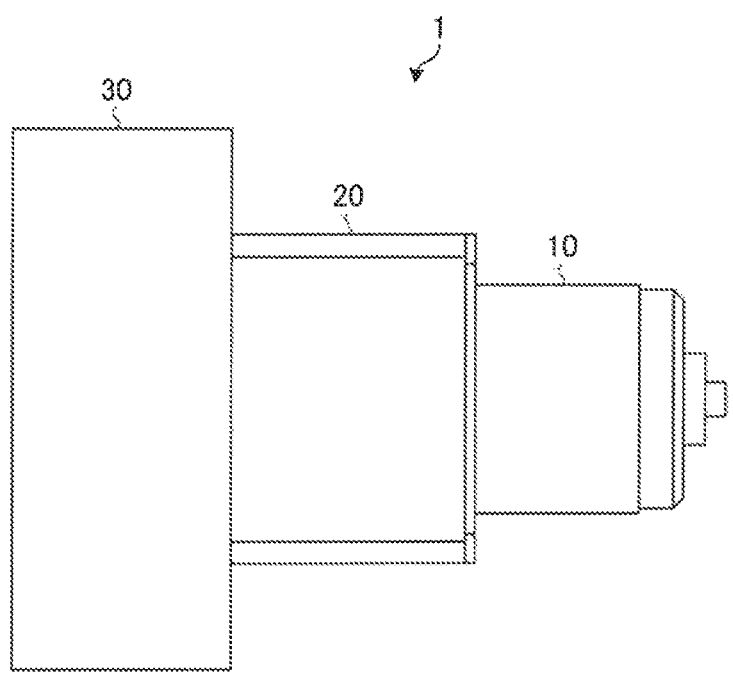
FIG. 2 is a first diagram for describing the blood pump shown in FIG. 1.
Figure 3:
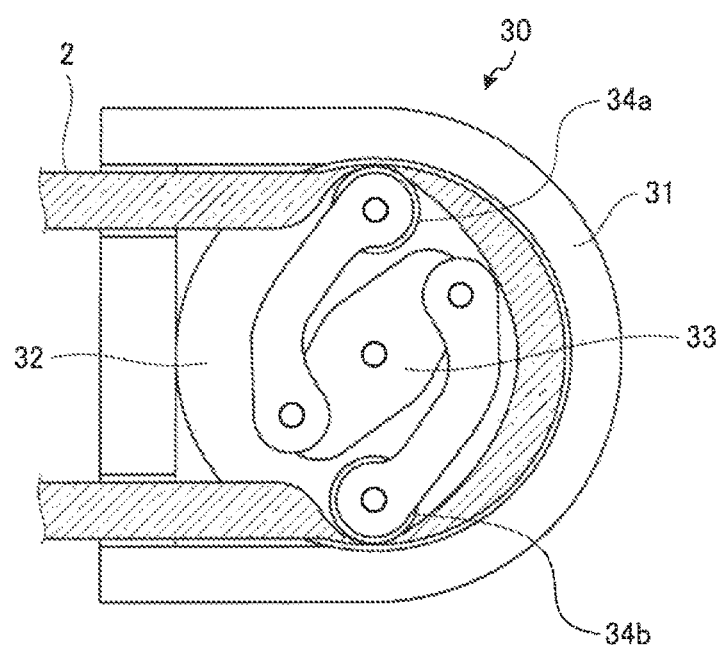
FIG. 3 is a second diagram for describing the blood pump shown in FIG. 1.

FIGS. 2 and 3 are diagrams for explaining the blood pump 1 shown in FIG. 1. The blood pump 1 includes a motor apparatus 10, a speed reducer 20, and a pump system 30, as shown in FIG. 2. FIG. 2 is a side view of the blood pump 1 shown in FIG. 1, and FIG. 3 shows the blood pump 1 shown in FIG. 1 and viewed from the side facing the pump system 30.

In FIG. 2, the motor apparatus 10 is a drive source that supplies a rotor 32 in the pump system 30 with rotational drive force via the speed reducer 20. The motor apparatus 10 has a motor 11, which will be described later. The speed reducer 20 is connected to the rotating shaft of the motor apparatus 10 (motor 11) and reduces the rotational speed of the rotating shaft of the motor 11 in accordance with a predetermined speed reduction ratio. The pump system 30 is connected to the rotating shaft (output shaft) of the speed reducer 20.

The pump system 30 includes a housing 31, a rotor 32, a roller support 33, a roller 34a, and a roller 34b, as shown in FIG. 3. The housing 31 has an internal space that accommodates the tube 2 and the rotor 32. The tube 2 is disposed along the arc-shaped inner circumferential wall surface of the housing 31. The rotor 32 is connected to the rotating shaft (output shaft) of the speed reducer 20.

The roller support 33 is connected to the rotor 32 and rotates when the rotor 32 rotates. The roller 34a and the roller 34b are attached to the opposite ends of the roller support 33. The roller support 33 rotatably supports the roller 34a and the roller 34b, which press the tube 2. The roller 34a and the roller 34b rotate when the roller support 33 rotates. That is, the roller 34a and the roller 34b rotate when driven by the motor apparatus 10 (motor 11) to press the tube 2, which is disposed along the inner circumferential wall surface of the housing 31, so as to deliver the liquid (blood) in the tube 2.

Figure 4:
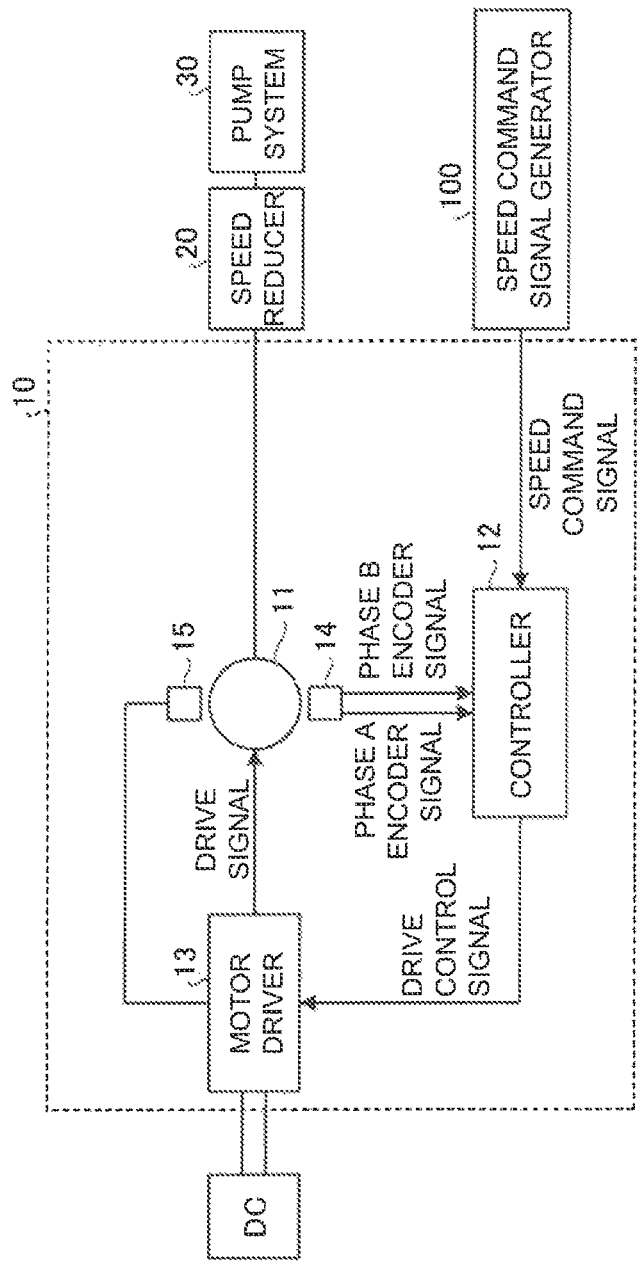
FIG. 4 is a block diagram showing an example of a configuration of a motor apparatus shown in FIG. 2.

FIG. 4 is a block diagram showing an example of the configuration of the motor apparatus 10 shown in FIG. 2. The motor apparatus 10 includes the motor 11, a controller 12, a motor driver 13, an encoder (example of position detector) 14, and a Hall element 15, as shown in FIG. 4.

The motor 11 is connected to the pump system 30 via the speed reducer 20. The motor 11 is, for example, a three-phase brushless DC motor. The motor 11 is driven and controlled by a motor drive controlling apparatus including the controller 12 and the motor driver 13. The motor drive controlling apparatus may further include the encoder 14 and the Hall element 15.

The motor driver 13 is connected to a DC power supply (see DC in FIG. 4), produces a drive signal in response to input of a drive control signal (which will be described later) produced by the controller 12, and outputs the drive signal to the motor 11. For example, the motor driver 13 includes a pre-drive circuit that is an analog integrated circuit and an inverter circuit. The inverter circuit outputs the drive signal to the motor 11 on the basis of an output signal outputted from the pre-drive circuit to conduct electricity to three armature coils provided in the motor 11. For example, the inverter circuit is configured so that a pair of series circuits provided at the opposite ends of the DC power supply and each formed of two switching elements is disposed for each of the phases of the three armature coils (U phase, V phase, and W phase). In each of the pair of two switching elements for each of the phases of the motor 11, the terminal for the phase of the motor 11 is connected to the point where the switching elements are connected to each other.

The pre-drive circuit produces the output signal for driving the inverter circuit under the control of the drive control signal (which will be described later) and outputs the output signal to the inverter circuit. As the output signal, for example, six kinds of switching signals corresponding to the switch elements of the inverter circuit are outputted. When the output signals are outputted, the switching elements corresponding to the output signals are turned on and off, so that the drive signal is outputted to the motor 11 to supply each of the phases of the motor 11 with electric power.

The Hall element 15 outputs a signal for detecting the rotational position of the rotating shaft of the motor 11 (rotor) (Hall signal) to the pre-drive circuit of the motor drive 13. The pre-drive circuit adjusts the switching timing of the ON/OFF actions of each of the switching elements of the inverter circuit on the basis of the Hall signal. The Hall element 15 may be replaced with a Hall IC.

The controller 12 is connected to a speed command signal generator 100, which is an external apparatus. The controller 12 is formed, for example, of a microprocessor (microprocessing unit: MPU). The controller 12 generates the drive control signal in response to input of a speed command signal. The speed command signal is a signal generated by the speed command signal generator 100 and is command information that specifies a target rotational speed of the rotating shaft of the motor 11. Specifically, the speed command signal is a pulse signal; the number of pulses of the pulse signal corresponds to the number of rotation steps, and the number of pulses per unit time corresponds to the rotational speed.

For example, the speed command signal generator 100 generates, as the speed command signal, a clock signal having a frequency according to the target rotational speed, for example, by using pulse frequency modulation (PFM) and outputs the clock signal to the controller 12. The controller 12 uses pulse width modulation (PWM) to generate, as the drive control signal, a PWM signal for rotating the rotating shaft of the motor 11 at a rotation speed corresponding to the clock signal.

The encoder 14 is an example of a position detector that detects the rotational position of the rotating shaft of the motor 11 (rotor). The encoder 14 outputs a pulse signal that synchronizes with the speed command signal (clock signal) and outputs a detection signal (encoder signal) based on the count of the pulses of the pulse signal. For example, when the rotating shaft of the motor 11 rotates at the rotational speed corresponding to the clock signal, the encoder 14 alternately outputs a signal from a phase A and a signal from a phase B at the rising edges of the clock signal. The counter in the encoder 14 counts the rising position/falling position of the Phase-A output waveform and the rising position/falling position of the Phase-B output waveform, and the encoder 14 outputs the resultant encoder signal.

The controller 12 generates the drive control signal (PWM signal) on the basis of the encoder signal outputted from the encoder 14 along with the speed command signal (clock signal) and outputs the drive control signal to the motor drive 13. For example, in response to the input of the clock signal, the controller 12 compares the count of the pulses of the clock signal with the count of the rising/falling positions in the encoder signal as long as the rotating shaft of the motor 11 rotates. In a case where the counts differ from each other, the controller 12 generates a PWM signal having a duty ratio changed so that the counts coincide with each other and outputs the PWM signal to the motor driver 13. During the rotation of the rotating shaft of the motor 11 in accordance with the input of the clock signal, the controller 12 may instead use the signal outputted from the Hall element 15 in place of the encoder signal outputted from the encoder 14 to control the rotational speed of the rotating shaft of the motor 11 in such a way that the rotational speed is maintained.

The speed reducer 20, which is provided in the blood pump 1 shown in FIG. 1, is disposed in the blood pump 1 to rotate the rotor 32 at a low speed and produce a large torque even in low-speed rotation. Some users, however, desire to operate the blood pump 1 at a rotational speed lower than that specified in the specifications of the motor 11.

In the present embodiment, to rotate the rotating shaft of the motor apparatus 10 (motor 11) at a low rotational speed that does not fall within the specifications, the controller 12 and the motor driver 13, which serve as the motor drive controlling apparatus, perform a motor drive controlling method described below.

The controller 12 repeatedly generates the drive control signal during a speed command signal input period and stops generating the drive control signal during a no speed command signal input period. The motor driver 13 repeatedly generates the drive signal and outputs the drive signal to the motor 11 (output step) in response to input of the drive control signal generated in the speed command signal input period and stops outputting the drive signal (stop step) when the generation of the drive control signal is stopped in the no speed command signal input period (repetition step).

Figure 5:
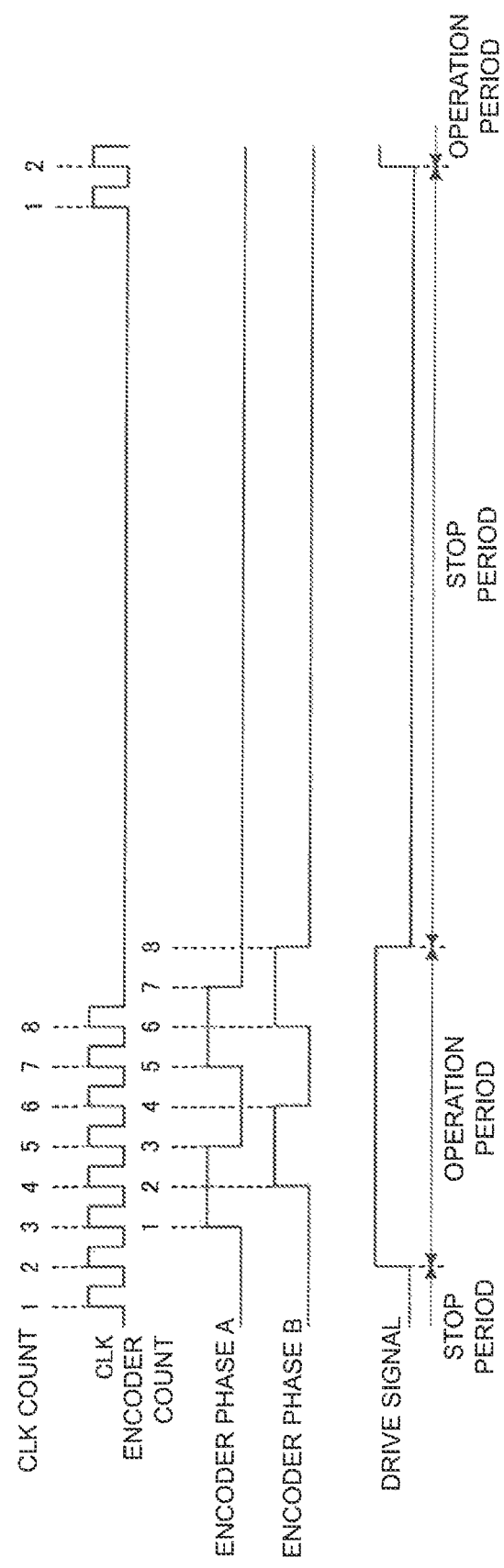
FIG. 5 is a first diagram for describing an intermittent action performed in the present embodiment.
Figure 6:
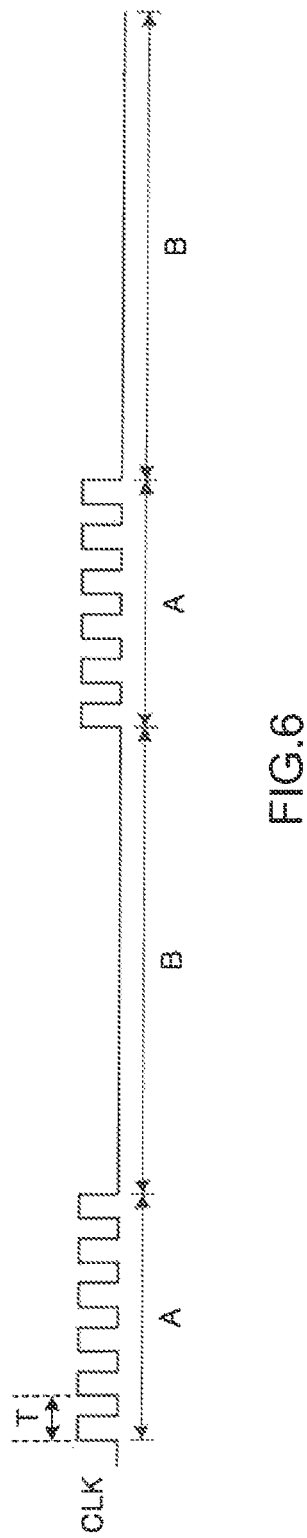
FIG. 6 is a second diagram for describing the intermittent action performed in the present embodiment.

As a result, the controller 12 repeats an operation period for which the rotating shaft of the motor 11 is rotated and a stop period for which the motor 11 is in a non-excited state and the rotating shaft of the motor 11 is therefore not rotated. That is, the motor 11 performs an intermittent action in which the operation period and the stop period are repeated. FIGS. 5 and 6 describe the intermittent action performed in the present embodiment.

In an exemplary timing chart shown in FIG. 5, the number of pulses of the clock signal (CLK) inputted for the operation period is set at 8 for ease of description. The speed command signal generator 100 starts outputting the clock signal, for example, in response to a user's instruction. The controller 12 generates the PWM signal in response to the inputted clock signal, and outputs the PWM signal to the motor driver 13. The motor driver 13 outputs the drive signal to the motor 11 on the basis of the PWM signal to drive the motor 11. In practice, 6 kinds of signals are outputted as the drive signal at respective points of time to the three phases of the motor 11. The "DRIVE SIGNAL" in FIG. 5 is drawn so that one pulse wave represents the period for which any of the 6 kinds of signals is outputted.

In response to the input of the drive signal, the operation period starts, and the rotating shaft of the motor 11 starts rotating. The encoder 14 alternately outputs the signal from the phase A and the signal from the phase B at the rising edges of the clock signal (see "ENCODER PHASE A" and "ENCODER PHASE B" in FIG. 5). The encoder 14 outputs the encoder signal representing the counter's count of the rising positions/falling positions of the phase-A output waveform and the rising positions/falling positions of the phase-B output waveform (see "ENCODER COUNT" in FIG. 5). The controller 12 performs typical control of maintaining the rotational speed at a fixed value on the basis of the clock signal and the encoder signal during the operation, as described above.

The speed command signal generator 100 stops generating the clock signal after outputted the 8 clock signals (see "CLK" in FIG. 5). The controller 12 stops generating the PWM signal in response to the termination of the input of the clock signal. The motor driver 13 then stops outputting the drive signal (see "DRIVE SIGNAL" in FIG. 5). As a result, the operation period ends and transitions to the stop period, and the motor 11 is therefore in the non-excited state and stops operating. When the motor 11 is not driven, the encoder 14 outputs an encoder signal having the same number of rising/falling positions as the number of pulses of the clock signal and stops outputting the encoder signal. The "ENCODER COUNT" in FIG. 5 shows that the encoder 14 outputs an encoder signal having 8 rising/falling positions, which is equal to the number of pulses of the clock signal and stops outputting the encoder signal. The motor 11 enters the stop period until the speed command signal generator 100 starts outputting the clock signal again.

How to set the intermittent action will next be described with reference to FIG. 6 and other figures. FIG. 6 shows that a clock signal (CLK) input period A and a no clock signal (CLK) input period B are alternately repeated in the intermittent action. The period A corresponds to the operation period, in which the motor 11 is in the excited state and the rotating shaft of the motor 11 therefore rotates, and the period B corresponds to the stop period, in which the motor 11 is in the non-excited state and the rotating shaft of the motor 11 therefore does not rotate. When the operation period and the stop period are alternately repeated, the rotational speed of the rotating shaft of the motor 11 per rotation is a second rotational speed lower than a first rotational speed corresponding to the speed command signal (clock signal).

The length of the operation period (period A) and the length of the stop period (period B) are set in accordance with the ratio between the first rotational speed and the second rotational speed. The second rotational speed is an ultralow rotational speed that is desired by the user and does not fall within the specifications of the motor 11. The first rotational speed is set at a lower-limit number of rotations per unit time that allows the rotating shaft of the motor 11 to keep rotating. The lower-limit number of rotations corresponds, for example, to the lower limit of the pulse width of the drive signal that can be generated by the motor driver 13.

An example of the setting of the operation period (period A) and the stop period (period B) will be described by using specific numerals. For example, assuming that the lower-limit number of rotations of the rotating shaft of the motor 11 is 45 rpm and the number of pulses outputted from the encoder 14 per rotation is 400, the number of pulses per second is "300 pps=(45 rpm*400)/60 sec," and the cycle of the pulses is "3.3 msec (=1/300)." Since the encoder 14 outputs an encoder signal that synchronizes with the clock signal, the number of pulses of the clock signal per second is also 300 pps, and the cycle of the pulses is 3.3 msec. In a case where the clock signal that specifies 45 rpm is inputted in synchronization with the encoder signal described above, T shown in FIG. 6 (interval between rising edges of clock signal) is 3.3 msec. The angle of rotation of the rotating shaft of the motor 11 corresponding to one pulse of the clock signal and the encoder signal is "0.9 degrees (=360 degrees/400)."

For example, when the rotational speed of the rotating shaft of the motor 11 desired by the user is 15 rpm, the ratio of the period A to the entire period (=period A+period B) is "15/45=1/3," resulting in "period A:period B=1:2." Further, in a case where the number of pulses in the operation period is fixed to 20 to fix the length of the operation period, the period A is set at "66 msec (=3.3 msec*20 pulses)," and the period B is set at "132 msec (=3.3 msec*40 pulses)."

Further, for example, in a case where the rotational speed desired by the user is 9 rpm, the ratio of the period A to the entire period is "9/45=1/5," resulting in "period A:period B=1:4." In the case where the number of pulses in the operation period is fixed to 20, the period A is set at "66 msec (=3.3 msec*20 pulses)," and the period B is set at "264 msec (=3.3 msec*80 pulses)."

As described above, in the present embodiment, adjustment of the length of the operation period and the length of the stop period in the intermittent action allows the motor 11 to be used at a rotational speed that is desired by the user and is lower than the lower-limit rotational speed of the rotating shaft of the motor 11.

In the example of the setting described above, during one rotation of the rotating shaft of the motor 11, the operation period and the stop period are repeated about 20 times to achieve an ultralow speed state that does not fall within the specifications of the motor 11. The example of the setting described above is merely presented by way of example, and the absolute values of the operation period and the stop period can be arbitrarily adjusted as long as the "ratio between the operation period and the stop period" is determined by the rotational speed desired by the user and the rotational speed corresponding to the clock signal. It is, however, noted that too short an operation period results in a small on-duty ratio of the drive signal, which causes the motor 11 not to be activated. It is therefore preferable to adjust the length of the operation period in such a way that the activation of the motor 11 is ensured.

On the other hand, prolonging the operation period also prolongs the stop period, resulting in non-smooth rotation of the rotating shaft of the motor 11. The rotational speed of the rotating shaft of the motor 11 is, however, reduced by the speed reducer 20. For example, in a case where the speed reduction ratio of the speed reducer 20 is 1/30, and the number of rotations of the rotating shaft of motor 11 is 15 rpm in the intermittent action, the rotor 32 rotates at a smaller number of rotations of 0.5 rpm. Even if the rotating shaft of the motor 11 does not rotate smoothly in the intermittent action, a rotation action smooth enough for the blood pump 1 is achieved by the speed reducer 20 interposed between the motor 11 and the blood pump 1.

The intermittent action described above is performed under the drive control of the controller 12 in coordination with input and no input of the speed command signal from the speed command signal generator 100. In the present embodiment, the speed command signal generator 100 is an external apparatus. For example, the user of the blood pump 1 refers to the example of the setting described above as a method for using the blood pump 1 and sets the speed command signal input period and the no speed command signal input period according to a desired rotational speed in the speed command signal generator 100. The user can thus cause the motor apparatus 10 to perform the intermittent action according to the present embodiment without changing the specifications of the motor apparatus 10.

In the case where a brushless DC motor (motor 11) is used in an ultralow speed state in the intermittent action, the rotational position of the rotating shaft of the motor 11 undesirably moves due to external factors during the stop period in the non-excited state. For example, in the pump system 30, variation in the torque of the motor 11 greatly varies in accordance with how much the tube 2 is pressed. Therefore, in the stop period, the torque variation resulting from the pressing operation of the tube 2 possibly cause the rotating shaft of the motor 11 to rotate in the direction in which the rotating shaft of the motor 11 rotates during the operation period (forward rotation) or in the direction opposite the direction during the operation period (reverse rotation).

When the torque variation causes positional shift in the stop period, correct actions of the motor 11 and the blood pump 1 cannot be ensured in the ultralow speed state. To avoid the undesirable situation, the controller 12 in the present embodiment performs a motor position holding function to keep a constant torque even in the stop period in the non-excited state.

That is, the controller 12, when it senses rotation of the rotating shaft of the motor 11 in a stop period, causes the motor 11 to transition from the non-excited state to the excited state and causes the rotational position of the rotating shaft of the motor 11 to return to the stop position where the motor 11 stopped operating when the preceding operation period ended. The controller 12 stores the rotational position of the rotating shaft of the motor 11 based on the detection signal (encoder signal) outputted from the encoder 14, for example, in an internal memory. The controller 12 stores the stop position where the motor 11 stopped operating when the preceding operation period ended on the basis of the count of the rising/falling positions of the encoder signal at the preceding operation period ending time.

The controller 12 then generates a drive control signal that causes the rotational position of the rotating shaft of the motor 11 to return to the stop position on the basis of the count of the rising/falling positions of the encoder signal outputted from the encoder 14 during the stop period. For example, the controller 12 compares the count of the rising/falling positions of the encoder signal outputted from the encoder 14 during the stop period with the count of the pulses of the clock signal inputted during the operation period to generate a drive control signal that causes the rotational position of the rotating shaft of the motor 11 to return to the stop position. The motor driver 13 thus generates a drive signal that causes the rotational position of the rotating shaft of the motor 11 to return to the stop position.

Figure 7:
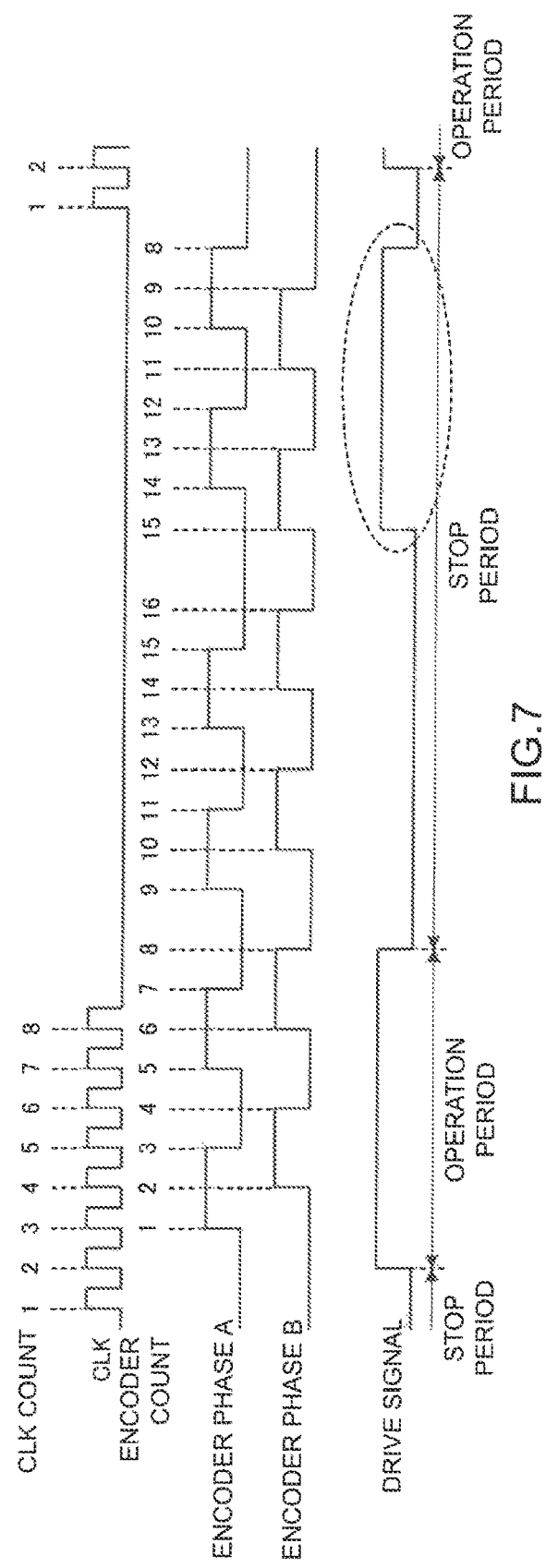
FIG. 7 is a diagram showing an example of a motor position holding function according to the present embodiment.

A specific example of the motor position holding function will be described below with reference to FIGS. 7 to 10. FIG. 7 shows an example of the motor position holding function according to the present embodiment. FIG. 7 shows a motor position holding function performed in the case where the intermittent action described with reference to FIG. 5 is performed.

An example shown in FIG. 7 shows that rotation of the rotating shaft of the motor 11 due to an external factor during a stop period causes the count of the pulses of the encoder signal to increase by 8 from "8" at the operation period ending time to "9, 10, . . . , 15, 16." The increase means that the rotating shaft of the motor 11 rotated during the stop period by the amount corresponding to the count of 8 in the forward direction. In the case where the number of pulses per rotation of the encoder 14 is 400, as in the example of the setting described above, the count of 1 of the encoder signal corresponds to 0.9 degrees. In other words, the rotating shaft of the motor 11 rotated by 7.2 degrees in the forward direction during the stop period in FIG. 7.

The controller 12 then generates a drive control signal that causes the rotating shaft of the motor 11 to rotate in the reverse direction by the count of 8 and outputs the drive control signal to the motor driver 13. The motor driver 13 then outputs a drive signal that causes the rotating shaft of the motor 11 to return to the stop position (see dotted circle in FIG. 7). As a result, the rotating shaft of the motor 11 rotates in the reverse direction, and the count of the pulses of the encoder signal outputted from the encoder 14 decreases by the count of 8 from "16" to "15, 14, . . . , 9, 8" and returns to the count of "8" corresponding to the stop position.

In the example shown in FIG. 7, the controller 12 is set so as to perform the motor position holding function when the absolute value of the difference between the count of the pulses of the clock signal (CLK COUNT) and the count of the pulses of the encoder signal (ENCODER COUNT) is "a threshold=8." The controller 12 then moves the rotational position of the rotating shaft of the motor 11 by the count of 8 in the reverse direction when "CLK COUNT<ENCODER COUNT." Although not shown, when "CLK COUNT>ENCODER COUNT," the controller 12 moves the rotational position of the rotating shaft of the motor 11 by the count of 8 in the forward direction.

Figure 8:
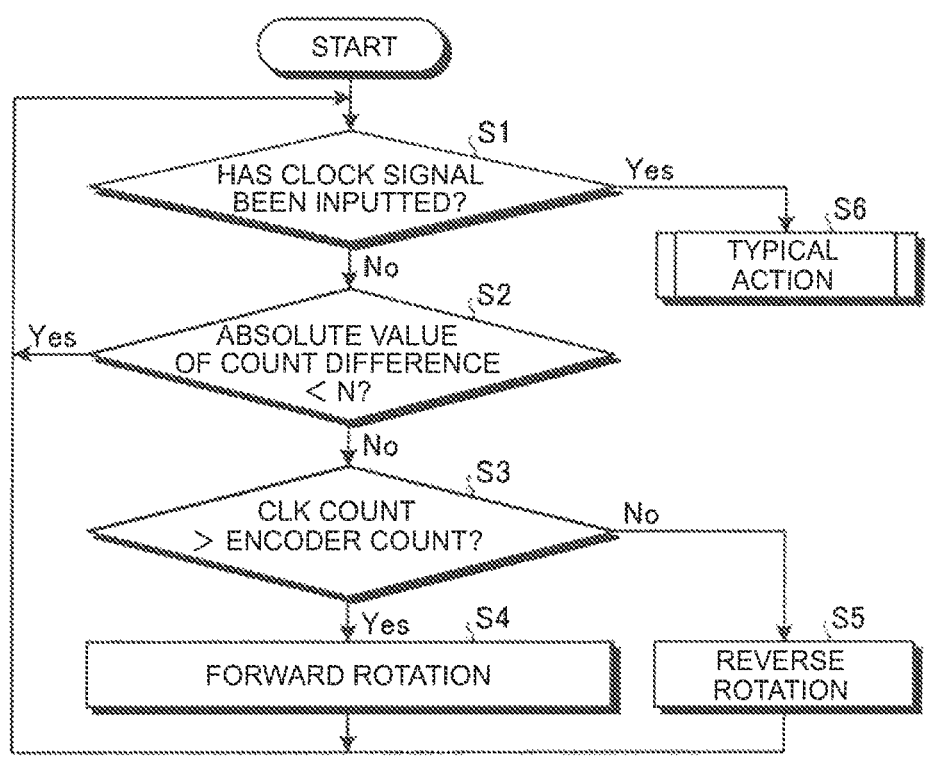
FIG. 8 is a flowchart for describing processes carried out by the motor position holding function shown in FIG. 7.

FIG. 8 is a flowchart for describing processes carried out by the motor position holding function shown in FIG. 7. In the flowchart of FIG. 8, the processes carried out by the motor position holding function shown in FIG. 7 by way of example are described under the condition of "the threshold=N" (N≥1). The controller 12 evaluates whether or not the clock signal has been inputted (step S1), as shown in FIG. 8. When the clock signal has been inputted (Yes in step S1), the controller 12 causes the motor 11 to perform a typical action (step S6). The typical action is the rotating action of the motor 11 in the operation period.

On the other hand, when no clock signal has been inputted (No in step S1), the controller 12 evaluates whether or not the absolute value of the count difference is smaller than N (step S2). When, the absolute value of the count difference is smaller than N (Yes in step S2), the controller 12 returns to step S1, where the controller 12 evaluates whether or not the clock signal has been inputted.

On the other hand, when the absolute value of the count difference is greater than or equal to than N (No in step S2), the controller 12 evaluates whether or not CLK COUNT is greater than ENCODER COUNT (step S3). When the CLK COUNT is greater than ENCODER COUNT (Yes step S3), the controller 12 controls the motor 11 to cause the rotating shaft thereof to rotate in the forward direction (step S4). In step S4, the controller 12 controls the motor 11 to cause the rotating shaft thereof to rotate by the amount corresponding to the count of N in the forward direction.

On the other hand, when the CLK COUNT is smaller than ENCODER COUNT (No step S3), the controller 12 controls the motor 11 to cause the rotating shaft thereof to rotate in the reverse direction (step S5). In step S5, the controller 12 controls the motor 11 to cause the rotating shaft thereof to rotate by the amount corresponding to the count of N in the reverse direction. After the process in step S4 or S5 is carried out, the controller 12 returns to step S1, where the controller 12 evaluates whether or not the clock signal has been inputted.

Figure 9:
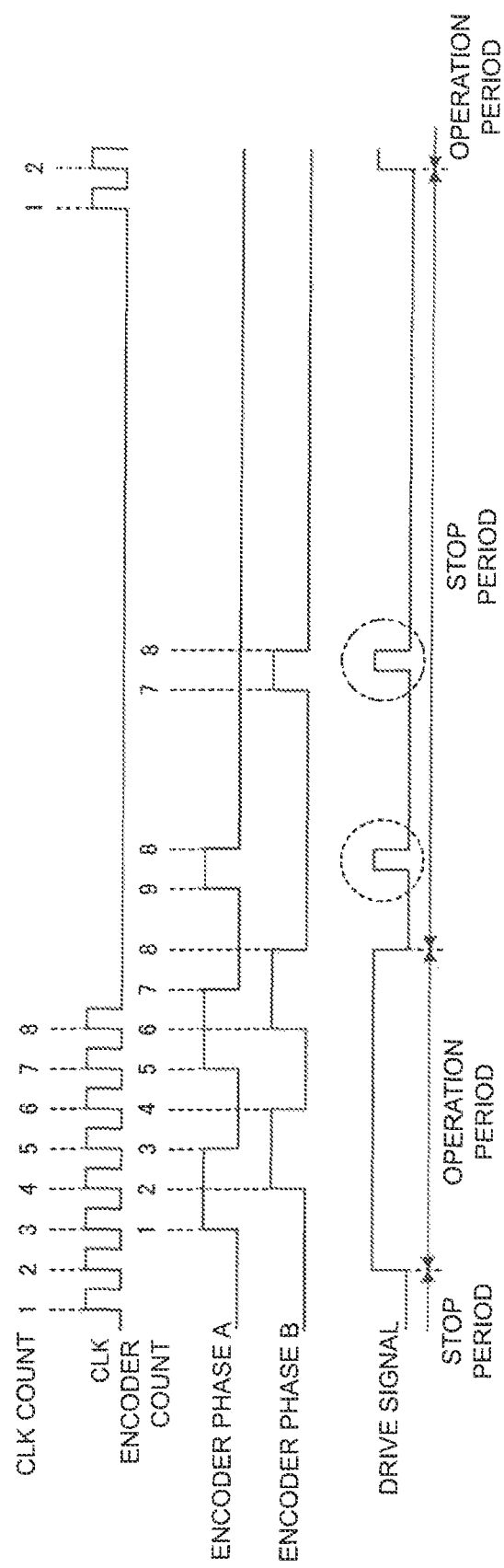
FIG. 9 is a diagram showing another example of the motor position holding function according to the present embodiment.

An example of the motor position holding function different from the example shown in FIGS. 7 and 8 will be described with reference to FIG. 9 and other figures. FIG. 9 shows another example of the motor position holding function according to the present embodiment. FIG. 9 shows a motor position holding function performed when the intermittent action described with reference to FIG. 5 is performed. FIG. 9 shows the process of performing the motor position holding function whenever the count difference becomes "1" under the condition of "N=1."

In the example shown in FIG. 9, rotation of the rotating shaft of the motor 11 due to an external factor during a stop period increases the count of the pulses of the encoder signal by 1 from "8", which is the count at the operation period ending time, to "9". The increase means that the rotating shaft of the motor 11 rotated during the stop period by the amount corresponding to the count of 1 (0.9 degrees) in the forward direction. The controller 12 then generates a drive control signal that causes the rotating shaft of the motor 11 to rotate by the amount corresponding to the count of 1 in the reverse direction and outputs the drive control signal to the motor driver 13. The motor driver 13 then outputs a drive signal that causes the rotational position of the rotating shaft of the motor 11 to return to the stop position (see dotted circle in FIG. 9). As a result, the rotating shaft of the motor 11 rotates in the reverse direction, and the count of the pulses of the encoder signal outputted from the encoder 14 decreases by 1 count from 9 to 8 and returns to the count "8" corresponding to the stop position.

The example shown in FIG. 9 then shows that rotation of the rotating shaft of the motor 11 due to an external factor during a stop period causes the count of the pulses of the encoder signal to decrease by 1 from "8" to "7". The decrease means that the rotating shaft of the motor 11 rotated during the stop period by the amount corresponding to the count of 1 (0.9 degrees) in the reverse direction. The controller 12 then generate a drive control signal that causes the rotating shaft of the motor 11 to rotate by the amount corresponding to the count of 1 in the forward direction and outputs the drive control signal to the motor driver 13. The motor driver 13 then outputs a drive signal that causes the rotational position of the rotating shaft of the motor 11 to return to the stop position (see chained circle in FIG. 9). As a result, the rotating shaft of the motor 11 rotates in the forward direction, and the count of the pulses of the encoder signal outputted from the encoder 14 increases by 1 from 7 to 8 count and returns to the count "8" corresponding to the stop position.

Figure 10:
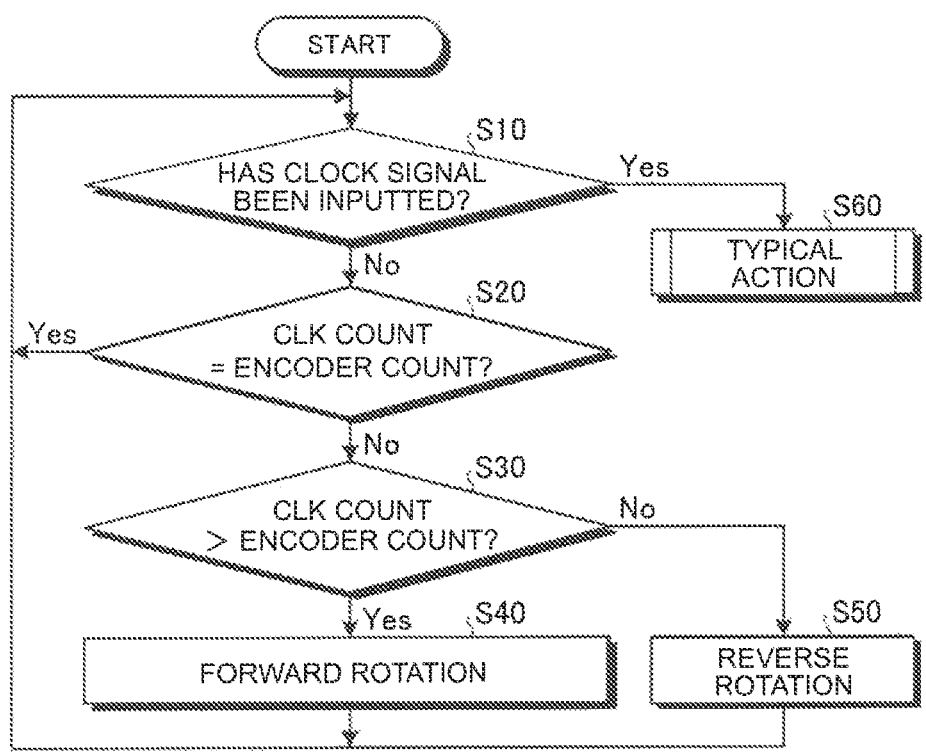
FIG. 10 is a flowchart for describing processes carried out by the motor position holding function shown in FIG. 9.

FIG. 10 is a flowchart for describing processes carried out by the motor position holding function shown in FIG. 9. The controller 12 evaluates whether or not the clock signal has been inputted (step S10), as shown in FIG. 10. When the clock signal has been inputted (Yes in step S10), the controller 12 causes the motor 11 to perform the typical action (step S60).

On the other hand, when no clock signal has been inputted (No in step S10), the controller 12 evaluates whether or not CLK COUNT is equal to ENCODER COUNT (step S20). When they are equal to each other (Yes in step S20), the controller 12 returns to step S10, where the controller 12 evaluates whether or not the clock signal has been inputted.

On the other hand, when they are not equal to each other (No in step S20), the controller 12 evaluates whether or not CLK COUNT is greater than ENCODER COUNT (step S30). When CLK COUNT is greater than ENCODER COUNT (Yes in step S30), the controller 12 controls the motor 11 to cause the rotating shaft thereof to rotate in the forward direction (step S40). In step S40, the controller 12 controls the motor 11 to cause the rotating shaft thereof to rotate by the amount corresponding to the count of 1 in the forward direction.

On the other hand, when CLK COUNT is smaller than ENCODER COUNT (No in step S30), the controller 12 controls the motor 11 to cause the rotating shaft thereof to rotate in the reverse direction (step S50). In step S50, the controller 12 controls the motor 11 to cause the rotating shaft thereof to rotate by the amount corresponding to the count of 1 in the reverse direction. After the process in step S40 or S50 is carried out, the controller 12 returns to step S10, where the controller 12 evaluates whether or not the clock signal has been inputted.

In the present embodiment, the motor position holding function described above allows elimination of positional shift due to the torque variation in the stop period in the non-excited state, whereby a stable ultralow speed state can be achieved. In particular, in the blood pump 1, in which the torque thereof greatly varies in accordance with how much the tube 2 is pressed, performing the motor position holding function can suppress the torque variation and therefore ensure the correct action of the blood pump 1 in the ultralow speed state. Further, the motor position holding function described above allows the rotational position of the rotating shaft of the motor 11 to return to the stop position even when the rotating shaft of the motor 11 having transitioned from the operation period (excited state) to the stop period (non-excited state) rotates due to moment of inertia. The value of threshold (N) may be configured to be changeable by the user even in a case where a fixed value is set in the controller 12. Further, the controller 12 may carry out the process of decreasing the threshold when the counts during the stop period greatly vary and increasing the threshold when the counts do not greatly vary. Further, in a case where the threshold can be set over a limited range, the rate of variation in the counts can be reduced by increasing the resolution of the encoder.

In the present embodiment, since the motor position holding function described above can maintain the rotational position of the rotating shaft of the motor 11 even by allowing the motor 11 to be in the non-excited state in the stop period, the power consumption can be lowered as compared with a case where the rotational position of the rotating shaft of the motor 11 is maintained by causing the motor 11 to be in the excited state even in the stop period.

The above description has been made with reference to the case where the speed command signal generator 100 is an external apparatus. In the present embodiment, the speed command signal generator 100 may instead be disposed as the motor drive controlling apparatus in the motor apparatus 10.

The above description has been made with reference to the case where the motor 11 is a brushless DC motor. The motor drive controlling method descried in the present embodiment can be used with any motor including a position detector that outputs a pulse signal that synchronizes with a clock signal and capable of rotational speed control based on the clock signal.

The above description has been made with reference to the case where the blood pump 1, which delivers the blood in the tube 2, is an example of a tube pump. Instead, the motor drive controlling method described in the embodiment can be used, for example, with a tube pump that delivers physiological saline or any other liquid.

The embodiment described above is not intended to limit the present disclosure. An embodiment in which the components described above are combined with one another as appropriate falls within the scope of the present disclosure. Further, a person skilled in the art can easily conceive of further effects and variations of the embodiment. Therefore, a wider aspect of the present disclosure is not limited to the embodiment described above but can be changed in a variety of manners.

What is claimed is:

1. A motor drive controlling apparatus comprising:
    a controller that generates a drive control signal in response to input of a speed command signal; and
    a motor driver that generates a drive signal in response to input of the drive control signal and outputs the drive signal to a motor, wherein the motor comprises a lower-limit rotational speed and, using the drive signal, the motor is operable at an operational rotational speed less than the lower-limit rotational speed of the motor, wherein:
    the controller repeatedly generates the drive control signal in a period during which the speed command signal is inputted and stops generating the drive control signal in a period during which the speed command signal is not inputted to repeat an operation period in which the motor performs rotational operation and a stop period in which the motor stops operating in a non-excited state,
    the speed command signal is a pulse signal, the number of the pulse signals per unit of time corresponding to a first rotational speed, and
    the controller repeats the operation period and the stop period to set the rotational speed of the motor per rotation at a second rotational speed lower than the first rotational speed corresponding to the speed command signal, so that the operational rotational speed of the motor, that is less than the lower-limit rotational speed of the motor, occurs using a combination of one or more repeated operation periods with one or more repeated stop periods.

2. The motor drive controlling apparatus according to claim 1, wherein the motor is a brushless DC motor.

3. The motor drive controlling apparatus according to claim 1, wherein a length of the operation period and a length of the stop period are set based on a ratio between the first rotational speed and the second rotational speed.

4. The motor drive controlling apparatus according to claim 1, wherein the first rotational speed is a lower-limit number of rotations per unit time that allows the motor to keep performing the rotational operation.

5. The motor drive controlling apparatus according to claim 4, wherein the lower-limit number of rotations corresponds to a lower-limit of a pulse width of a drive signal allowed to be generated by the motor driver.

6. The motor drive controlling apparatus according to claim 1, wherein the speed command signal is generated by an external apparatus and outputted to the controller.

7. The motor drive controlling apparatus according to claim 1, further comprising a speed command signal generator that generates the speed command signal.

8. A motor drive controlling apparatus comprising:
    a controller that generates a drive control signal in response to input of a speed command signal; and
    a motor driver that generates a drive signal in response to input of the drive control signal and outputs the drive signal to a motor, wherein the motor comprises a lower-limit rotational speed and, using the drive signal, the motor is operable at an operational rotational speed less than the lower-limit rotational speed of the motor,
    wherein the controller repeatedly generates the drive control signal in a period during which the speed command signal is inputted and stops generating the drive control signal in a period during which the speed command signal is not inputted to repeat an operation period in which the motor performs rotational operation and a stop period in which the motor stops operating in a non-excited state, so that the operational rotational speed of the motor, that is less than the lower-limit rotational speed of the motor, occurs using a combination of one or more repeated operation periods with one or more repeated stop periods, and
    wherein when the controller senses the rotational operation of the motor in the stop period, the controller changes a state of the motor from the non-excited state to an excited state to cause a position in the rotational operation of the motor to return to a stop position where the motor stops operating when the operation period ends.

9. The motor drive controlling apparatus according to claim 8,
    further comprising a position detector that detects the position in the rotational operation of the motor,
    wherein the position detector outputs a pulse signal that synchronizes with the speed command signal and outputs a detection signal based on a count of pulses of the pulse signal, and
    the controller stores the position in the rotational operation of the motor based on the detection signal outputted from the position detector.

10. The motor drive controlling apparatus according to claim 9, wherein the controller generates a drive control signal that causes the position in the rotational operation of the motor to return to the stop position based on a count based on the detection signal outputted from the position detector during the stop period.

11. A motor drive controlling method comprising:
an output step of generating a drive signal in response to input of a drive control signal generated in a period during which a speed command signal is inputted and outputting the drive signal to a motor, the speed command signal being a pulse signal, the number of the pulse signals per unit of time corresponding to a first rotational speed, wherein the motor comprises a lower-limit rotational speed and, using the drive signal, the motor is operable at an operational rotational speed less than the lower-limit rotational speed of the motor;
a stop step of stopping the output of the drive signal when the generation of the drive control signal is stopped in a period during which the speed command signal is not inputted; and
a repetition step of repeating the output step and the stop step to repeat an operation period in which the motor performs rotational operation and a stop period in which the motor stops operating in a non-excited state,
wherein the repetition step repeats the operation period and the stop period to set the rotational speed of the motor per rotation at the second rotational speed lower than the first rotational speed corresponding to the speed command signal, so that the operational rotational speed of the motor, that is less than the lower-limit rotational speed of the motor, occurs using a combination of one or more repeated operation periods with one or more repeated stop periods.

12. A tube pump comprising:
a motor;
a roller that rotates when driven by a motor to press a tube so as to deliver a liquid in the tube; and
a motor drive controlling apparatus including a controller that generates a drive control signal in response to input of a speed command signal and a motor driver that generates a drive signal in response to input of the drive control signal and outputs the drive signal to the motor, wherein the motor comprises a lower-limit rotational speed and, using the drive signal, the motor is operable at an operational rotational speed less than the lower-limit rotational speed of the motor;
wherein:
the controller repeatedly generates the drive control signal in a period during which the speed command signal is inputted and stops generating the drive control signal in a period during which the speed command signal is not inputted to repeat an operation period in which the motor performs rotational operation and a stop period in which the motor stops operating in a non-excited state,
the speed command signal is a pulse signal, the number of pulse signals per unit of time corresponding to a first rotational speed, and
the controller repeats the operation period and the stop period to set the rotational speed of the motor per rotation at a second rotational speed lower than the first rotational speed corresponding to the speed command signal, so that the operational rotational speed of the motor, that is less than the lower-limit rotational speed of the motor, occurs using a combination of one or more repeated operation periods with one or more repeated stop periods.

* * * * *